(12) United States Patent
Cochran et al.

(10) Patent No.: US 11,848,097 B2
(45) Date of Patent: Dec. 19, 2023

(54) MACHINE LEARNING MODELS FOR AUTOMATED REQUEST PROCESSING

(71) Applicant: Evicore Healthcare MSI, LLC, Bluffton, SC (US)

(72) Inventors: William K. Cochran, Franklin, TN (US); Bijuna S. Pramila, Livingston, NJ (US); Han Van Vo, King of Prussia, PA (US); Hari C. Narayanan, Livingston, NJ (US); Navin Rai, Trumbull, CT (US)

(73) Assignee: Evicore Healthcare MSI, LLC, Bluffton, SC (US)

( * ) Notice: Subject to any disclaimer, the term of this patent is extended or adjusted under 35 U.S.C. 154(b) by 415 days.

(21) Appl. No.: 17/124,712

(22) Filed: Dec. 17, 2020

(65) Prior Publication Data

US 2023/0360778 A1    Nov. 9, 2023

(51) Int. Cl.

| | |
|---|---|
| *G16H 40/20* | (2018.01) |
| *G06N 20/00* | (2019.01) |
| *G16H 30/20* | (2018.01) |
| *G16H 30/40* | (2018.01) |
| *G16H 50/20* | (2018.01) |
| *G16H 15/00* | (2018.01) |
| *G16H 50/70* | (2018.01) |
| *G06Q 10/10* | (2023.01) |
| *G06Q 40/08* | (2012.01) |

(Continued)

(52) U.S. Cl.
CPC .............. *G16H 40/20* (2018.01); *G06N 20/00* (2019.01); *G06Q 10/10* (2013.01); *G06Q 40/08* (2013.01); *G06T 7/0012* (2013.01); *G16H 10/20* (2018.01); *G16H 15/00* (2018.01); *G16H 30/20* (2018.01); *G16H 30/40* (2018.01); *G16H 50/20* (2018.01); *G16H 50/70* (2018.01); *A61B 5/055* (2013.01); *A61B 6/032* (2013.01); *G06T 2207/20076* (2013.01); *G06T 2207/20081* (2013.01)

(58) Field of Classification Search
None
See application file for complete search history.

(56) References Cited

U.S. PATENT DOCUMENTS

| | | |
|---|---|---|
| 9,710,755 B2 | 7/2017 | Srivastava |
| 10,204,144 B2 | 2/2019 | De Mars |

(Continued)

*Primary Examiner* — Wei Wen Yang
(74) *Attorney, Agent, or Firm* — Harness IP

(57) ABSTRACT

A computerized method of automatically processing a medical imaging record using a machine learning model includes training a machine learning model prediction engine with historical medical imaging records, receiving a first medical imaging record from a first system, applying a set of specified approval criteria to the first medical imaging record to determine a provisional outcome, and in response to the provisional outcome being negative, selectively identifying an exception to the provisional outcome in response to input received by a user interface. In response to the exception not being identified, the method includes inputting a feature vector based on the first medical imaging record to the machine learning model prediction engine to generate a likelihood estimate, comparing the generated likelihood estimate to a target threshold, and in response to the generated likelihood estimate being greater than the target threshold, transmitting a signal indicating approval to the first system.

18 Claims, 6 Drawing Sheets

(51) Int. Cl.
*G16H 10/20* (2018.01)
*G06T 7/00* (2017.01)
*A61B 6/03* (2006.01)
*A61B 5/055* (2006.01)

(56) References Cited

U.S. PATENT DOCUMENTS

| | | |
|---|---|---|
| 10,417,737 B2 | 9/2019 | Park |
| 10,424,045 B2 | 9/2019 | Park |
| 10,445,658 B2 | 10/2019 | Salas |
| 10,679,325 B2 | 6/2020 | Park |
| 10,765,888 B2 | 9/2020 | Sjolund |
| 11,074,656 B2 | 7/2021 | Smith |
| 2012/0290319 A1 | 11/2012 | Saria |
| 2017/0316334 A1 | 11/2017 | Srivastava |
| 2017/0372155 A1 | 12/2017 | Odry |
| 2018/0190377 A1 | 7/2018 | Schneemann |
| 2019/0122160 A1 | 4/2019 | Kolandaiswamy |
| 2019/0371450 A1 | 12/2019 | Lou |
| 2020/0013141 A1 | 1/2020 | Park |
| 2020/0074874 A1 | 3/2020 | Quinn |
| 2020/0135296 A1 | 4/2020 | Girshick |
| 2020/0334566 A1 | 10/2020 | Ron |
| 2020/0342335 A1 | 10/2020 | Burke |
| 2020/0405148 A1* | 12/2020 | Tran .................... A61B 3/0016 |
| 2021/0090694 A1* | 3/2021 | Colley ................... G16B 40/00 |
| 2021/0358050 A1 | 11/2021 | Smith |

* cited by examiner

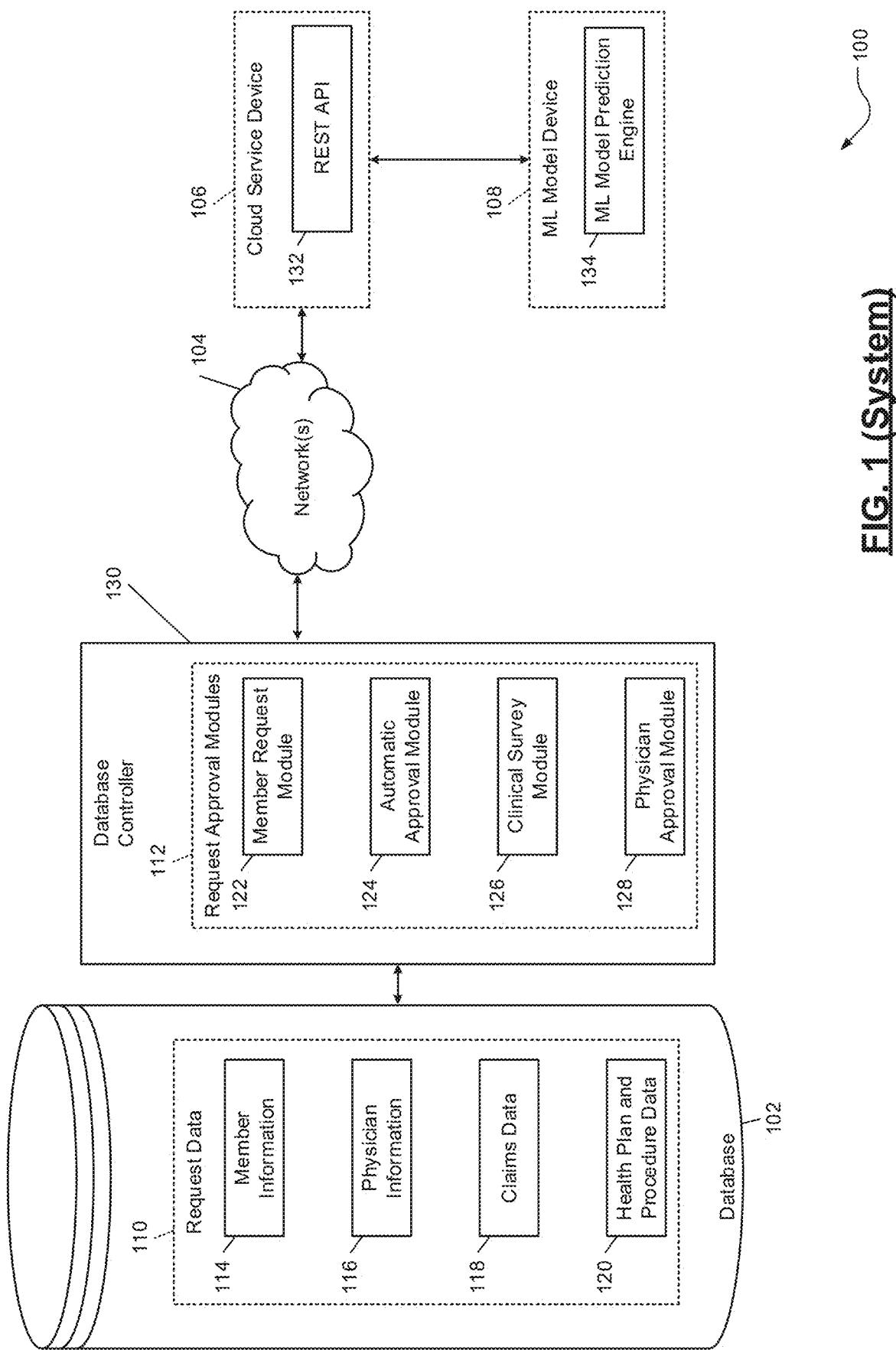
FIG. 1 (System)

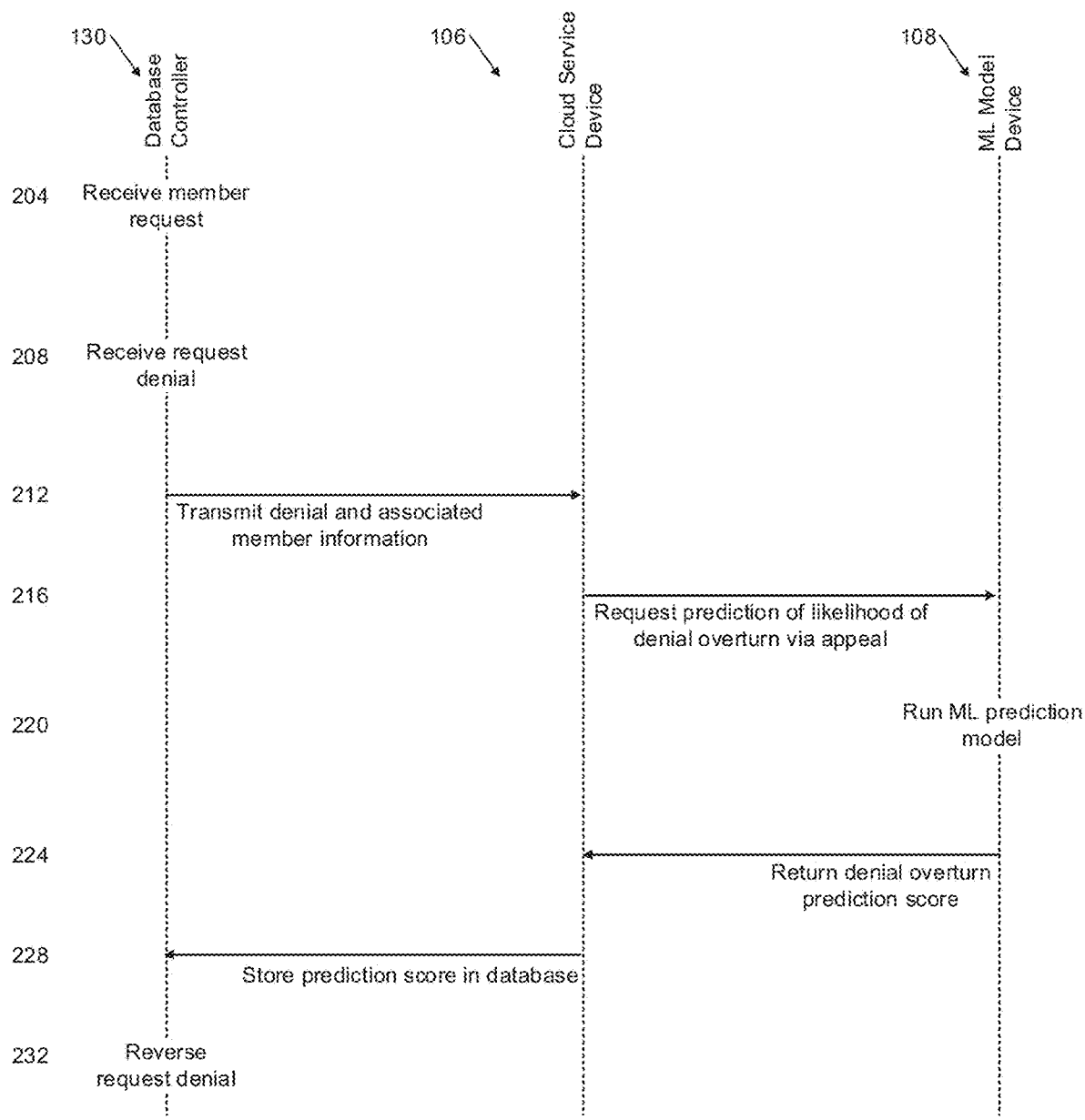
FIG. 2 (System MSC)

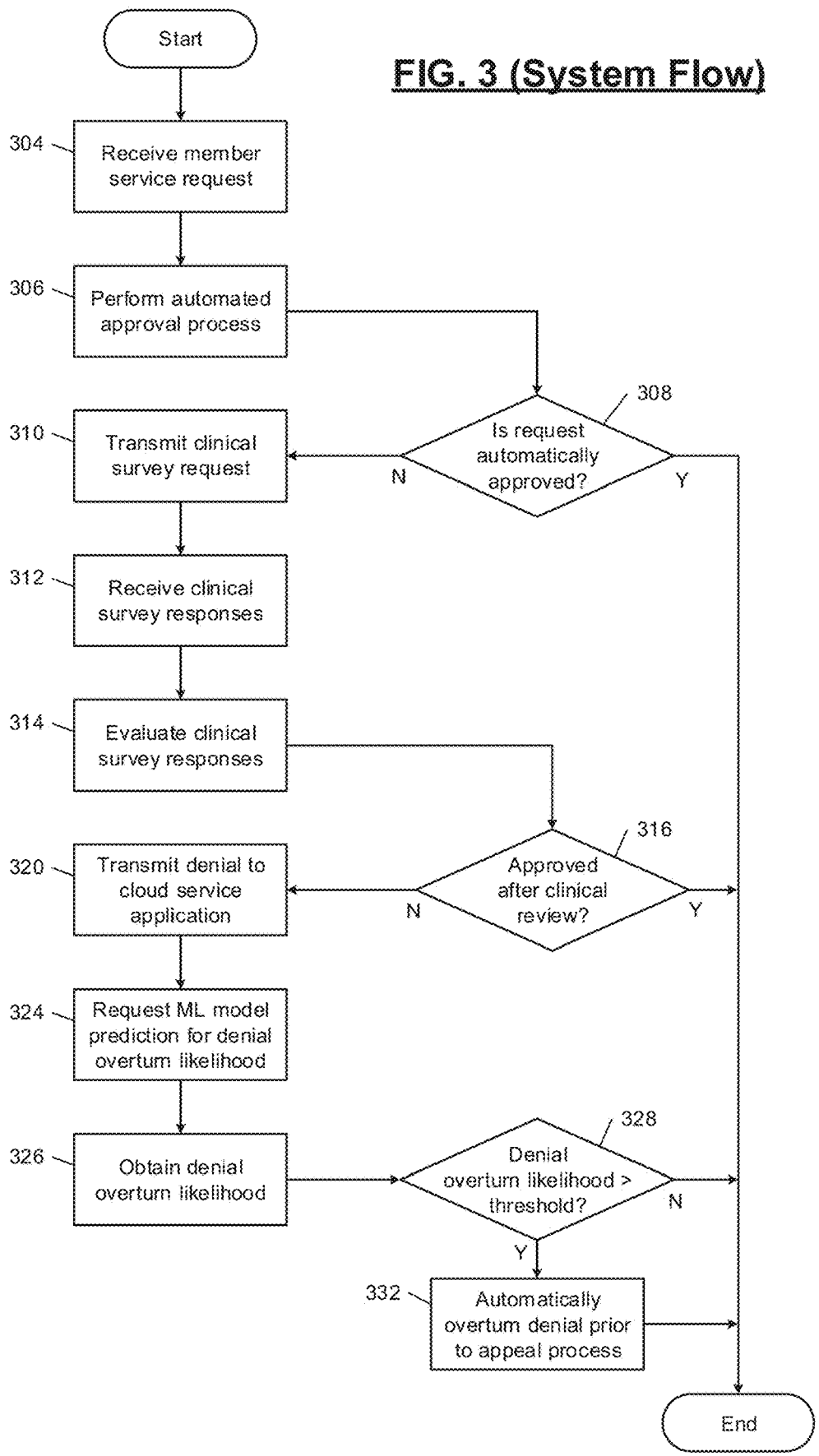

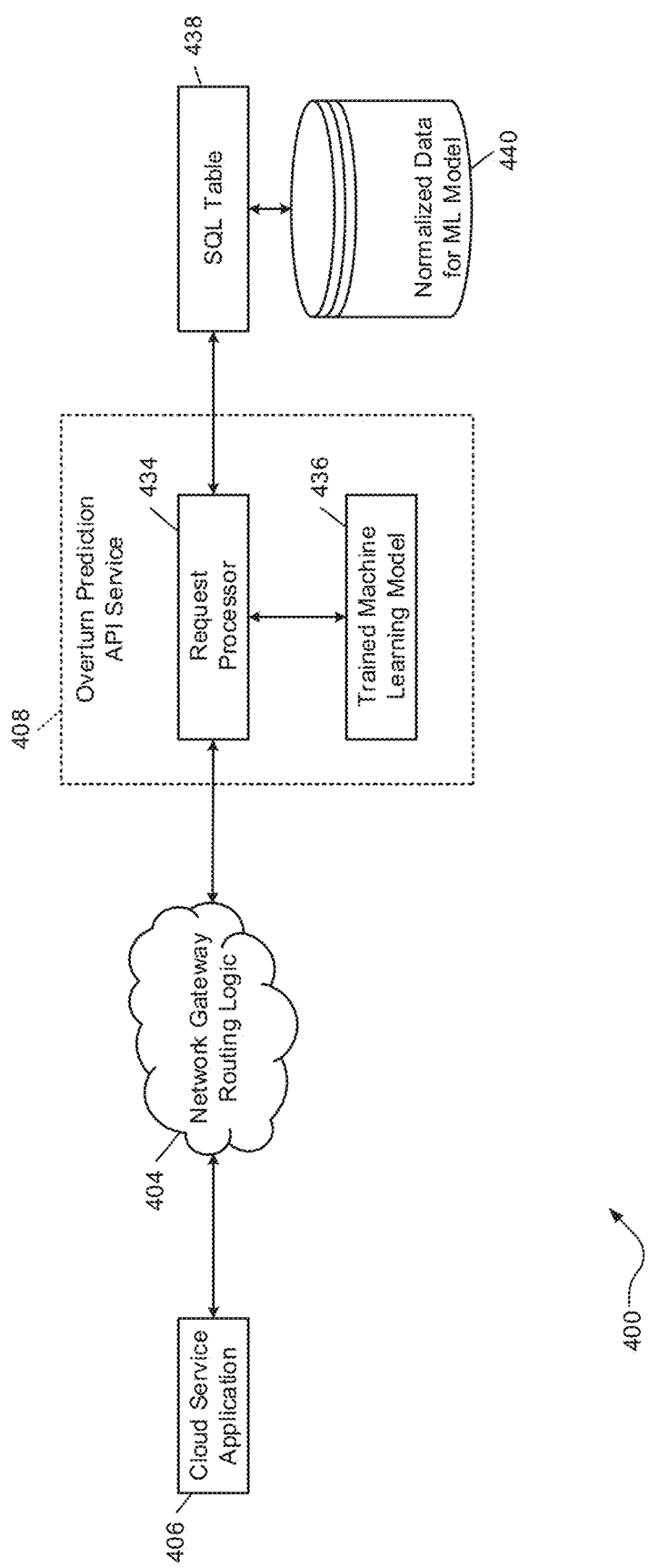
FIG. 4 (API Architecture)

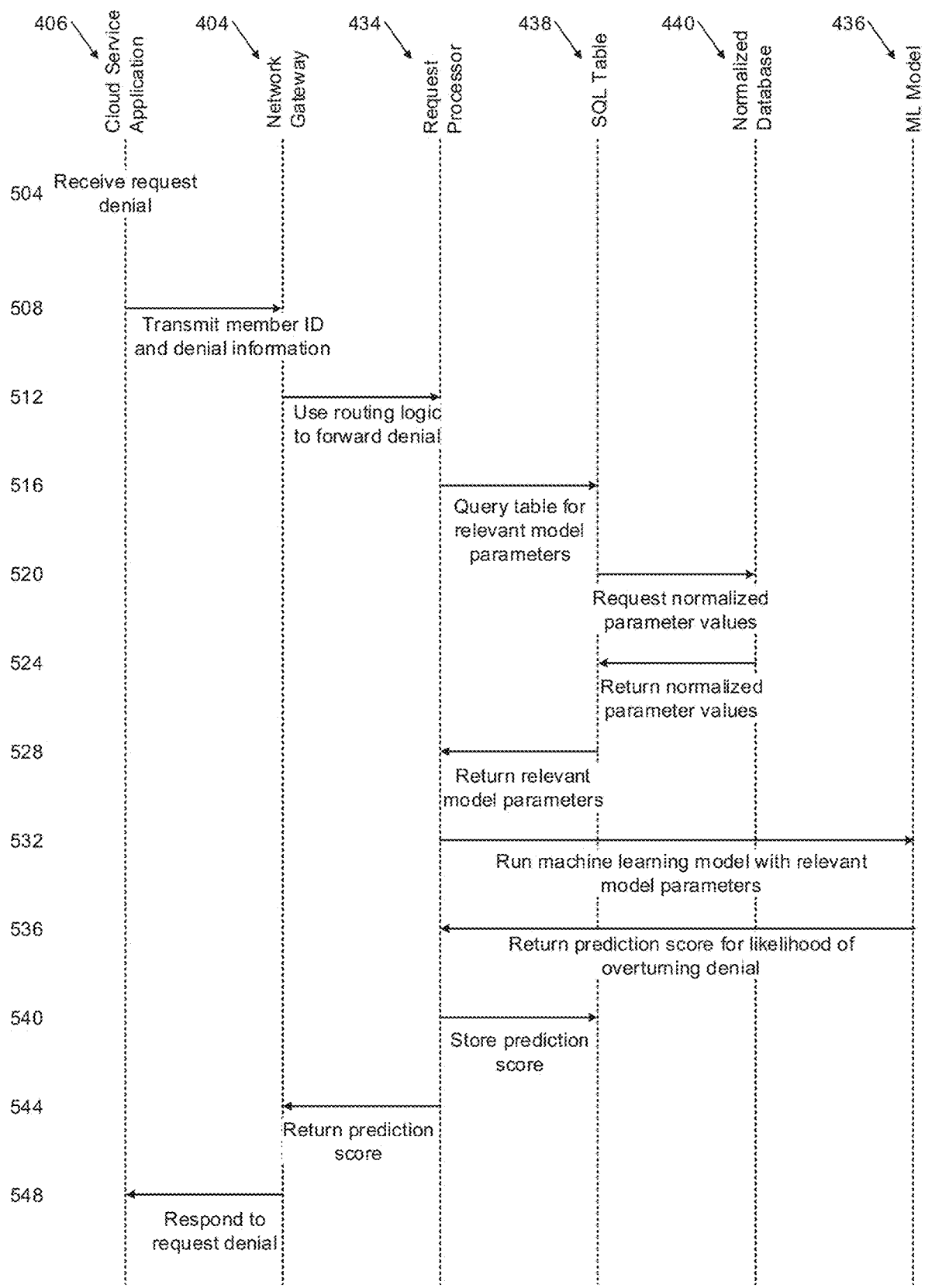
FIG. 5 (API MSC)

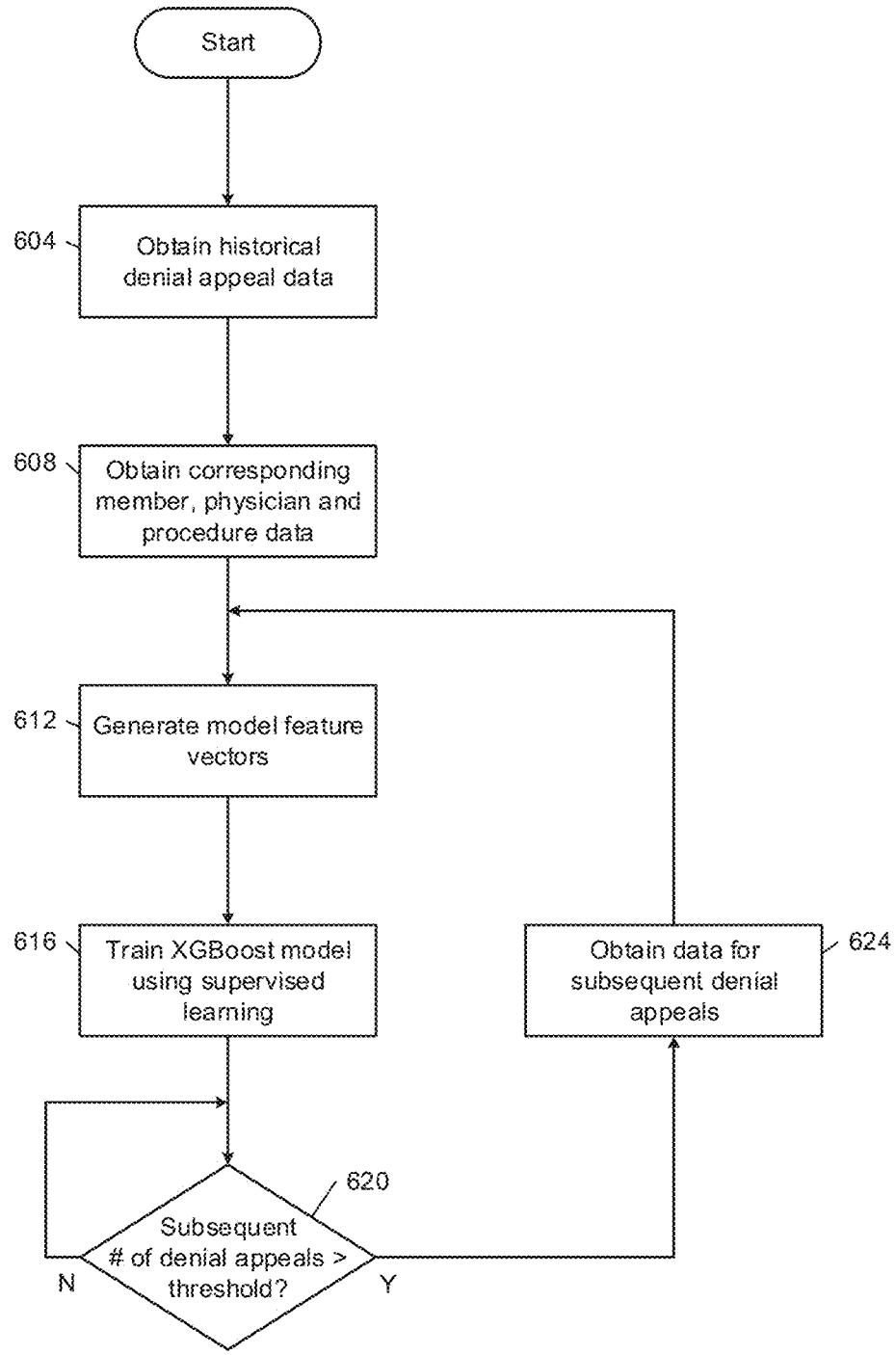
FIG. 6 (Model Training Flow)

MACHINE LEARNING MODELS FOR AUTOMATED REQUEST PROCESSING

FIELD

The present disclosure relates to machine learning models for automated request processing.

BACKGROUND

Patients in the healthcare setting sometimes request diagnostic imaging, such as magnetic resonance imaging (MRI) scans or computerized tomography (CT) scans, as part of their course of treatment or to potentially identify health issues. An administrator or physician may review a patient's imaging request to determine whether the request should be approved. For example, the administrator or physician may determine whether the imaging request is necessary or appropriate for the patient's care and current health situation, whether the patient's condition would benefit from the imaging request such that the healthcare insurance provider should cover the cost imaging, or whether the use of the imaging resources is justified, etc.

During review, the patient's imaging request may be denied. For example, the administrator or physician may initially determine that the patient's current health condition does not require the specific imaging request, or that the imaging request would not be beneficial. In that case, the patient may initiate an appeal process to attempt to overturn the denial of the imaging request. The appeal process can be time-consuming, often taking between sixty and ninety days or longer, and increases costs for the administrators to review the appeal process. In addition, the appeal process may increase patient complaints, or healthcare provider or insurer complaints.

The background description provided here is for the purpose of generally presenting the context of the disclosure. Work of the presently named inventors, to the extent it is described in this background section, as well as aspects of the description that may not otherwise qualify as prior art at the time of filing, are neither expressly nor impliedly admitted as prior art against the present disclosure.

SUMMARY

A computerized method of automatically processing a medical imaging record using a machine learning model includes training a machine learning model prediction engine with historical medical imaging records to generate likelihood estimates, according to historical feature vector inputs generated from the historical medical imaging records, and receiving a first medical imaging record from a first system. The first medical imaging record is specific to a first entity. The method includes applying a set of specified approval criteria to the first medical imaging record to determine a provisional outcome, in response to the provisional outcome being positive, transmitting a signal indicating approval to the first system, and in response to the provisional outcome being negative, providing data related to the first medical imaging record to a user interface, and selectively identifying an exception to the provisional outcome in response to input received by the user interface. In response to the exception being identified, the method includes transmitting the signal indicating approval to the first system. In response to the exception not being identified, the method includes generating a feature vector based on the first medical imaging record, inputting the feature vector to a machine learning model prediction engine, generating, by the machine learning model prediction engine, a likelihood estimate based on the feature vector, comparing the generated likelihood estimate to a target threshold, and in response to the generated likelihood estimate being greater than the target threshold, transmitting the signal indicating approval to the first system.

In other features, the method includes, in response to the exception not being identified, transmitting the data related to the first medical imaging record via a representational state transfer (REST) application programming interface (API) of a cloud service device in communication with the machine learning model prediction engine. In other features, the method includes storing, in a normalized database, parameters associated with multiple entities of a specified group including the first entity, performing, on a periodic basis, updating and normalization of the stored parameters for each of the multiple entities, and generating the likelihood estimate includes obtaining normalized parameters associated with the first entity from the normalization database, and generating the likelihood estimate according to the obtained normalized parameters.

In other features, obtaining the normalized parameters includes querying a structured query language (SQL) data structure in communication with the normalized database, and the method further includes storing the generated likelihood estimate in the SQL data structure. In other features, the method includes obtaining request data associated with the first medical imaging record, the request data includes at least one of entity information data associated with the first entity, physician information data of a physician associated with the first entity, claims data associated with the first entity, health plan data associated with the first entity, and procedure data associated with the first medical imaging record, and generating the feature vector includes generating the feature vector based at least in part on the request data associated with the first medical imaging record.

In other features, the method includes receiving an appeal notification from the first entity at the first system. The signal indicating approval is transmitted to the first system prior to receiving the appeal notification. In other features, the method includes receiving an appeal notification from the first entity at the first system, and in response to receiving, at the first system, the appeal notification and the signal indicating approval, responding to the appeal notification according to the signal indicating approval.

In other features, selectively identifying an exception to the provisional outcome includes receiving, at the user interface, clinical survey responses from a reviewing entity, and evaluating the received clinical survey responses to determine whether an exception to the provisional outcome is identified by the reviewing entity. In other features, training the machine learning model prediction engine includes generating the historical feature vector inputs according to at least one of historical entity data, historical physician data, historical procedure data, and historical appeal data, each of which are associated with the historical medical imaging records, and supplying the historical feature vector inputs to the machine learning model prediction engine to train the machine learning model of the machine learning model prediction engine to generate likelihood estimates using supervised learning. In other features, the machine learning model comprises an extreme gradient boosting (XGBoost) model. In other features, the method includes converting the XGBoost model to a linear model including multiple parameters for generating the likelihood estimate.

A computer system for automatically processing a medical imaging record using a machine learning model includes memory hardware configured to store a machine learning model prediction engine, historical medical imaging records, and computer-executable instructions, and processor hardware configured to execute the instructions. The instructions include training the machine learning model prediction engine with the historical medical imaging records to generate likelihood estimates, according to historical feature vector inputs generated from the historical medical imaging records, and receiving a first medical imaging record from a first system. The first medical imaging record is specific to a first entity. The instructions include applying a set of specified approval criteria to the first medical imaging record to determine a provisional outcome, and in response to the provisional outcome being positive, transmitting a signal indicating approval to the first system. In response to the provisional outcome being negative, the method includes providing data related to the first medical imaging record to a user interface, and selectively identifying an exception to the provisional outcome in response to input received by the user interface. In response to the exception being identified, the instructions include transmitting the signal indicating approval to the first system. In response to the exception not being identified, the instructions include generating a feature vector based on the first medical imaging record, inputting the feature vector to a machine learning model prediction engine, generating, by the machine learning model prediction engine, a likelihood estimate based on the feature vector, comparing the generated likelihood estimate to a target threshold, and in response to the generated likelihood estimate being greater than the target threshold, transmitting the signal indicating approval to the first system.

In other features, the instructions further include, in response to the exception not being identified, transmitting the data related to the first medical imaging record via a representational state transfer (REST) application programming interface (API) of a cloud service device in communication with the machine learning model prediction engine. In other features, the instructions further include storing, in a normalized database, parameters associated with multiple entities of a specified group including the first entity, performing, on a periodic basis, updating and normalization of the stored parameters for each of the multiple entities, and the generating the likelihood estimate includes obtaining normalized parameters associated with the first entity from the normalization database, and generating the likelihood estimate according to the obtained normalized parameters.

In other features, the obtaining the normalized parameters includes querying a structured query language (SQL) data structure in communication with the normalized database, and the instructions further include storing the generated likelihood estimate in the SQL data structure. In other features, the instructions further include obtaining request data associated with the first medical imaging record, the request data includes at least one of entity information data associated with the first entity, physician information data of a physician associated with the first entity, claims data associated with the first entity, health plan data associated with the first entity, and procedure data associated with the first medical imaging record, and the generating the feature vector includes generating the feature vector based at least in part on the request data associated with the first medical imaging record.

In other features, the instructions further include receiving an appeal notification from the first entity at the first system. The signal indicating approval is transmitted to the first system prior to receiving the appeal notification. In other features, the instructions further include receiving an appeal notification from the first entity at the first system, and in response to receiving, at the first system, the appeal notification and the signal indicating approval, responding to the appeal notification according to the signal indicating approval.

In other features, the selectively identifying an exception to the provisional outcome includes receiving, at the user interface, clinical survey responses from a reviewing entity, and evaluating the received clinical survey responses to determine whether an exception to the provisional outcome is identified by the reviewing entity. In other features, the training the machine learning model prediction engine includes generating the historical feature vector inputs according to at least one of historical entity data, historical physician data, historical procedure data, and historical appeal data, each of which are associated with the historical medical imaging records, and supplying the historical feature vector inputs to the machine learning model prediction engine to train the machine learning model of the machine learning model prediction engine to generate likelihood estimates using supervised learning.

Further areas of applicability of the present disclosure will become apparent from the detailed description, the claims, and the drawings. The detailed description and specific examples are intended for purposes of illustration only and are not intended to limit the scope of the disclosure.

BRIEF DESCRIPTION OF THE DRAWINGS

The present disclosure will become more fully understood from the detailed description and the accompanying drawings.

FIG. 1 is a functional block diagram of an example system including a machine learning model for automated processing of medical imaging requests.

FIG. 2 is message sequence chart illustrating example interactions between components of the system of FIG. 1.

FIG. 3 is a flowchart depicting an example process for automatically processing a medical imaging request.

FIG. 4 is a functional block diagram of an example API architecture for implementing a machine learning model for automated processing of medical imaging requests.

FIG. 5 is a message sequence chart illustrating example interactions between components of the system of FIG. 4.

FIG. 6 is a flowchart depicting an example process for training a machine learning model to predict a likelihood estimate of overturning a denied imaging request.

In the drawings, reference numbers may be reused to identify similar and/or identical elements.

DETAILED DESCRIPTION

Healthcare patients sometimes initiate appeals when their requests for diagnostic imaging are denied. If an appeal is successful and the initial request denial is overturned, it may be considered as a waste of the time and resources that were used during the appeal process, such that it would have been desirable to avoid the appeal altogether if possible. In various implementations disclosed herein, a machine learning model is used to predict when a denial of an imaging request will likely be overturned. If the predicted likelihood of overturning the denial is high, the appeal process may be shortened or eliminated altogether, which can save money and improve the attitude of the patient with regard to the imaging request process. For example, an imaging request denial may be overturned to preemptively to allow the request prior to any appeal being filed or carried out, which may lead to fewer complaints by patients, healthcare providers and insurers, and provide a smoother overall process with reduced costs.

Automated Imaging Request Processing System

FIG. 1 is a functional block diagram of an example system 100 including a machine learning model for automated processing of medical imaging requests, which includes a database 102. While the system 100 is generally described as being deployed in a computer network system, the database 102 and/or components of the system 100 may otherwise be deployed (for example, as a standalone computer setup). The system 100 may include a desktop computer, a laptop computer, a tablet, a smartphone, etc.

As shown in FIG. 1, the database 102 stores request data 110. The request data 110 may include any suitable data associated with a request for medical services by an entity (such as a patient). For example, an oncology patient may requests an MRI or CT scan. The request for medical services may be considered as a medical imaging record (such as a database record of a patient's request for a medical imaging service).

FIG. 1 illustrates example elements of the request data 110, including member information 114, physician information 116, claims data 118, and health plan and procedure data 120. In various implementations, other types of request data 110 may be stored, and the database 102 may store other types of data as well. The member information 114, physician information 116, claims data 118, and health plan and procedure data 120, may be located in different physical memories within the database 102, such as different random access memory (RAM), read-only memory (ROM), a non-volatile hard disk or flash memory, etc. In some implementations, one or more of the member information 114, physician information 116, claims data 118, and health plan and procedure data 120, may be located in the same memory (such as in different address ranges of the same memory).

As described further below, the member information 114 may include any suitable information about a patient that is submitting a request for healthcare services, such as a diagnostic medical imaging request. For example, the member information 114 may include the patient's name, age, sex, medical history, prior medical claims, etc. The patient may provide any of their member information 114, and details of their imaging request, via any suitable user device for displaying text and receiving input form a user, including a desktop computer, a laptop computer, a tablet, a smartphone, etc. The user device may access the database 102 directly, or may access the database 102 through one or more networks 104 and the database controller 130. Example networks may include a wireless network, a local area network (LAN), the Internet, a cellular network, etc.

The database controller 130 may include one or more request approval modules 112. For example, request approval modules 112 illustrated in FIG. 1 include a member request module 122, an automatic approval module 124, a clinical survey module 126, and a physician approval module 128. The member request module 122 may include any suitable user interface or submission form that allows the patient to request a diagnostic service such as an MM or CT diagnostic scan.

Referring back to the database 102, the request data 110 includes physician information 116. The physician information 116 may include any suitable data about a physician involved in care of the patient, or involved in the decision of whether to permit the patient's imaging request. For example, the physician information 116 may include data about a history of imaging requests for patients of the physician, how often imaging requests that are denied by the physician are overturned on appeal, etc.

Similarly, the claims data 118 may include historical data about claims associated with the imaging request, such as prior claims of the patient that submitted the request, prior claims associated with other patients of the physician that is reviewing the request, etc. The health plan and procedure data 120 may include any suitable data about the specific imaging request that the patient submitted, such as a cost of the imaging request, the time and resources needed to schedule or implement the request, the relationship of the request to different health conditions of the patient, diagnosis codes, procedure codes, etc.

Each of the different pieces of request data 110 may be used by the request approval modules 112 in order to determine whether the patient's initial imaging request should be approved or denied. For example, the automatic approval module 124 may be include a computer system or program that analyzes the data of the imaging request, such as data obtained from the member request module 122, to automatically determine whether the request should be approved (such as when the data associated with the request meets specific predefined approval criteria).

For example, if the imaging request is consistent with a known health condition of the patient, if the imaging request has been previously labeled as authorized by a physician overseeing the patient's care, if the patient has a history of approved requests for this type of imaging service, or if the patient has not requested this type of service within a threshold time period or below a threshold count of requests, the automatic approval module 124 may automatically approve the imaging request. In various implementations, control may apply a set of specified approval criteria to a medical imaging record to determine a provisional outcome, such as determining whether an imaging request of the medical imaging record should be automatically approved. A positive provisional outcome may indicate that the imaging request is approved, while a negative provisional outcome may indicate that the imaging request is not approved.

If the automatic approval module 124 is unable to automatically approve the request (such as because the request did not meet specified approval criteria thresholds), the clinical survey module 126 may be used to allow a nurse or other healthcare professional to provide a manual review of the patient's request. For example, the nurse or practitioner may review the request to determine whether a patient's request should be approved even though the request did not automatically meet the approval criteria of the automatic approval module 124. In the event that the nurse or administrator does not approve the request via the clinical survey module 126, a physician approval module 128 may be used by a physician to provide a final review of the patient's imaging request. The physician approval module 128 may provide a user interface for the physician to review details of the imaging request and provide an approval or denial of the request according to whether all details of the imaging request are appropriate or suitable for the patient.

The clinical survey module 126 and/or the physician approval module 128 may be used to selectively identify an exception to the provisional outcome from the automatic approval module 124. For example, a reviewing entity (such as a nurse or physician) may identify an exception such that the imaging request should be approved, even if the automatic approval module 124 generated a negative provisional outcome.

As shown in FIG. 1, a cloud service device 106 includes a representational state transfer (REST) API 132 that is in communication with a machine learning model device 108, which includes a machine learning model prediction engine 134. As described further below, if the patient's imaging request is denied, such as via a final denial received at the physician approval module 128, details of the denied imaging request may be provided to the machine learning model prediction engine 134 via the REST API 132 of the cloud service device 106. In various implementations, the cloud service device 106 and the REST API 132 may be arranged via a subscription in an Azure cloud system (which may include a Cosmos database), or another suitable cloud processing system.

For example, the details of the denied request may be provided to the machine learning model prediction engine 134 may include elements from the request data 110, such as member information 114 about the patient that requested the imaging diagnostic service, physician information 116 about the physician that denied the request, and claims data 118 and health plan and procedure data 120 associated with prior claims of the patient or additional details of the specific imaging service that was requested. The machine learning model prediction engine 134 may then predict whether the denial is likely to be overturned, according to the received denial details and request data 110. Although FIG. 1 illustrates one example implementation of the database 102, database controller 130, cloud service device 106 and machine learning model device 108, in other implantations the database 102, database controller 130, cloud service device 106 and machine learning model device 108, may be distributed in any suitable manner across one or more servers, memories, processors, etc.

FIG. 2 is a message sequence chart illustrating example interactions between the database controller 130, the cloud service device 106, and the machine learning model device 108, during automated processing of a patient's imaging request by the system 100. As shown in FIG. 2, the database controller 130 receives a member request at line 204, such as via the member request module 122 of the database controller 130. The member request may be any a request for any suitable healthcare diagnostic service, such as an oncology patient requesting an Mill or CT scan.

At line 208, the database controller 130 receives a request denial. For example, the patient's imaging request may be denied by the automatic approval module 124, the clinical survey module 126, and the physician approval module 128. If the patient's imaging request is finally denied, the database controller 130 transmits the denied request and associated member information to the cloud service device 106, at line 212. For example, the database controller 130 may transmit information about the denial along with request data 110, including member information 114, physician information 116, claims data 118, and health plan and procedure data 120.

After receiving the denial information, the cloud service device 106 requests a prediction from the machine learning model device 108, of a likelihood estimate that the denial will be overturned via an appeal, at line 216. The machine learning model device 108 then runs the machine learning model at line 220. For example, the machine learning model device 108 may input the denial details and any request data 110 received from the cloud service device 106 into the machine learning model, and run the machine learning model to provide an output indicative of a likelihood estimate that the denied member request will be overturned during an appeal process. At line 224, the machine learning model device 108 returns a denial overturn prediction score to the cloud service device 106.

At line 228, the cloud service device 106 stores the received prediction score with the database controller 130. The database controller 130 may then determine whether the prediction score is above a target threshold, such as greater than an eighty or ninety percent likelihood of overturning the denied imaging request. If the database controller 130 determines the prediction score is above the target threshold, the database controller 130 may reverse the denial at line 232. In that case, the database controller 130 may eliminate the appeal process in order to save costs and time, and increase patient satisfaction.

FIG. 3 is a flowchart depicting an example process for automatically processing a medical imaging request. At 304, control begins by receiving the member service request, such as via the member request module 122. At 306, control performs an automated approval process 306. For example, the automatic approval module 124 may be used to determine whether the patient request meets specified criteria for automatic approval, such as the request being consistent with a health condition of the member, the request being flagged for approval by a physician caring for the patient, etc.

At 308, control determines whether the request has been automatically approved, such as by the automatic approval module 124. If so, the process ends because the member's service request has already been approved. If the request is not automatically approved at 308, control proceeds to 310 to transmit a clinical survey request. For example, control may transmit a clinical survey request to a nurse, administrator or physician, such as via the clinical survey module 126 or the physician approval module 128. The nurse, administrator or physician may then review the member's service request manually, and provide a response indicating whether the request should be approved.

At 312, control receives the clinical survey responses from the nurse, administrator or physician, and evaluates the clinical survey responses at 314. For example, control may receive the clinical survey responses from the clinical survey module 126 or the physician approval module 128. At 316, control determines whether the service request has been approved according to the clinical review by the nurse, administrator or physician. If so, the process ends because the request is approved.

If control determines at 316 that the clinical review denied the request, control proceeds to 320 to transmit the denial to the cloud service application. For example, control may transmit the denial to the cloud service device 106. At 324, control requests the machine learning model to generate a prediction of a likelihood that the denial will be overturned. In the system 100, the REST API 132 of the cloud service device 106 may transmit the request to the machine learning model device 108, in order for the machine learning model prediction engine 134 to generate the prediction of the likelihood of the request denial being overturned during appeal.

Control obtains the denial overturn likelihood at 326. For example, the REST API 132 of the cloud service device 106 may receive a likelihood output from the machine learning model prediction engine 134 of the machine learning model device 108. Control then determines at 328 whether the denial overturn likelihood is greater than a threshold. For example, if the likelihood is not greater than eighty or ninety percent (or any other suitable threshold), the process may end without proceeding further. In this situation, control has determined that there is not a significant enough likelihood that the denial will be overturned during appeal, so control will allow the appeal process to play out normally to see if the denial will be confirmed during the appeal process.

If control determines at 328 that the likelihood of the denial being overturned is greater than the threshold, control proceeds to 332 to automatically overturn the denial prior to the appeal process (such as prior to receiving an appeal notification from the patient). In this case, control determined that there is a strong likelihood that the request denial will be overturned on appeal, so control saves time and cost by automatically overturning the denial before the appeal process is initiated or completed (such as by generating or transmitting an indicator that the denial should be overturned, or an indicator that the appeal request status should be set as approved). Alternatively, in various implementations control may wait until an appeal is actually filed by the member before overturning the denial and approving the request. Control may perform the model prediction process asynchronously with respect to the appeal process, and only intervene in the denial appeal if the predicted likelihood of overturning the denial is above the threshold.

As one example implementation of the process, a rational decision tool plugin (RDT) pathway may be invoked in response to a physician denying a request, such as via the physician approval module 128. The RDT plugin may publish events to a subscriber API that consumes the events. Filters may be used for the events, such as filtering by healthcare provider, patient diagnosis, physician specialty, etc., which may be configurable in an Azure Cosmos database (or any other suitable database). In various implementations, the API may post a machine learning model payload, receive a prediction from the machine learning model, and save the output in the Azure Cosmos database. Each API transaction may be logged in the Azure Cosmos database. Azure Appinsight and Serilog may be used for logging and exception handling.

Machine Learning Model API Architecture

FIG. 4 is a functional block diagram of an example API architecture 400 for implementing a machine learning model for automated processing of medical imaging requests. As shown in FIG. 4, a cloud service application 406 is connected with an overturn prediction API service 408, via a network gateway routing logic 404. For example, the cloud service application 406 may supply details of a denied imaging request to the overturn prediction API service 408 via the network gateway routing logic. In various implementations, the cloud service application 406 may process requests via a Python application in an OpenShift container platform.

The overturn prediction API service 408 includes a request processor 434 and a trained machine learning model 436. The request processor 434 may include any suitable hardware and/or software modules to extract data from the request, in order to retrieve information needed for the trained machine learning model 436 to make a prediction of whether the request denial will be overturned on appeal. As explained further below, the request processor 434 is in communication with a structured query language (SQL) table 438, such as an SQL data structure which accesses normalized data for the machine learning model from a normalized database 440. Although FIG. 4 illustrates an SQL table 438, various implementations may use other suitable databases and interfaces.

The normalized database 440 may use nightly batch operations (or any other suitable period such as hours or weeks), to prepare normalized data for the trained machine learning model 436, such as via integration with a Teradata framework of the SQL table 438. For example, the data may be prepared using a Teradata ETL process implemented using a Python CCW library, which provides custom functions to connect to Teradata tables and run queries to extract results. Data may be exported from a Teradata table to an NAS drive, and then to a PostGreSQL table, such as the SQL table 438. The normalized database 440 may store normalized data that is needed to make potential predictions regarding denied imaging requests from eligible member populations in the CCW data. A FeatureTools Python library may be used to compute aggregated values for the normalized data. The request processor 434 may create inputs for the trained machine learning model 436 based on data from the cloud service application 406 and the normalized database 440.

After the trained machine learning model 436 processes the input to generate the prediction output, the prediction output is supplied to the request processor 434. The request processor 434 may then store the input request and the generated likelihood output to the SQL table 438 (such as a PostGreSQL table). Audit data may be captured for continuous evaluation of the model performance. The request processor 434 also provides a response via the API service to the cloud service application 406, using the network gateway routing logic 404.

In various implementations, the trained machine learning model 436 may include a DataRobot model service. For example, a trained DataRobot XGBoost model may be exported as a prime model that is a very close approximation of the original model. The prime model may include multiple variables based on the trained XGBoost model, and may facilitate faster real time scoring (because the prime model uses a more algebraic linear model with coefficient parameters). Some example parameters of the model may include a number of days since the last active treatment of the patient, a number of days since the first active treatment, a count of radiation treatments, a count of chemotherapy treatments, a sum of the total medical cost (TMC) of the patient over the last twelve months, a sum of emergency TMC for the patient over the last twelve months, a sum of the professional TMC for the patient over the last twelve months, concatenated procedure codes of procedures that the patient had over the last six months, primary and secondary diagnosis codes for the patient over the last six months, a sum of the TMC for the patient over the last six months, etc. In various implementations, other variables may be used, and different variables may have different weights in the model.

FIG. 5 is a message sequence chart illustrating example interactions between the cloud service application 406, the network gateway routing logic 404, the SQL table 438, the normalized database 440 and the trained machine learning model 436, during automated processing of a denied medical imaging request by the API architecture 400. At line 504, the cloud service device 106 receives a request denial. For example, the patient's imaging request and details associated with the denial of the request may be received by the cloud service application 406.

At 508, the cloud service application 406 transmits the member ID and information about the denied request to the network gateway routing logic 404. The network gateway routing logic 404 uses routing logic to forward the denial to the request processor 434, at line 512. At line 516, the request processor 434 queries the SQL table 438 for relevant model parameters.

The SQL table 438 requests normalized parameter values from the normalized database 440, at line 520, and the normalized database 440 then returns the requested normalized parameter values to the SQL table 438 at line 524. At line 528, the SQL table 438 returns the model parameters to the request processor 434, and the request processor 434 runs the trained machine learning model 436 with the relevant model parameters at line 532.

At line 536, the trained machine learning model 436 returns a prediction score indicating the likelihood that the denied request will be overturned during an appeal process. The request processor 434 than stores the prediction score in the SQL table 438, at line 540. At line 544, the request processor 434 returns a prediction score to the network gateway routing logic 404, and the network gateway routing logic 404 forwards the score to the cloud service application 406 at line 548, in order for the cloud service application 406 to determine whether the denied request should be overturned before appeal.

Machine Learning Model Training

FIG. 6 is a flowchart depicting an example process for training a machine learning model to predict a likelihood of overturning a denied imaging request. At 604, control begins by obtaining historical denial appeal data. For example, data may be obtained about historical events where a patient requested an imaging service and the request was denied. The historical event data may also include a determination of whether or not the request denial was eventually overturned on appeal. In various implementations, control may obtain historical feature vector inputs based on historical medical imaging requests, which may be associated with historical entity data, historical physician data, historical procedure data, historical appeal data, or any other suitable historical data for training the machine learning model.

At 608, control obtains corresponding data for the request, such as member information 114 of the patient that submitted the request, physician information 116 for the physician that denied the request, claims data 118 associated with the patient's prior medical claims, and health plan and procedure data 120 associated with the specific imaging service requested by the patient. At 612, control generates model feature vectors based on the historical denial appeal data and its corresponding member, physician and procedure information. Although FIG. 6 illustrates training the machine learning model using feature vector inputs, in various implementations the machine learning model may be trained by supplying input data to the machine learning model in any suitable format.

Control trains an extreme gradient boosting (XGBoost) model using supervised learning at 616. For example, control may supply the historical denial appeal data and its corresponding member, physician and procedure data, to the XGBoost model as an input. Control uses the determination of whether the historical appeal was successfully returned or not, in order to train the XGBoost model to predict whether future denials are likely to be overturned on appeal.

Although FIG. 6 illustrates an XGBoost model, various implementations may use any suitable machine learning models. In some implementations, the machine learning model service may test out multiple machine learning models on the historical data, and select the type of model that exhibits the closest accuracy in correctly predicting denial overturn likelihoods for the historical denial appeal data.

Once the XGBoost model is trained at 616, the XGBoost model may be used to predict subsequent denials as they are submitted by patients over time. Once enough subsequent denials and appeal processes have occurred, the machine learning model may be retrained based on the subsequent denial events. For example, at 620 control determines whether the subsequent number of request denials is greater than a threshold. The threshold may be any suitable number, such as at least ten subsequent request denials, at least one hundred subsequent request denials, at least one thousand request denials, etc. Although FIG. 6 illustrates comparing a number of request denials to a threshold, various implantations may use time periods instead of, or in combination with, total numbers of subsequent request denials. For example, the model may be retrained every week, every month, every year, etc.

If control determines at 620 that the subsequent number of request denials is less than the threshold, control waits for additional subsequent request denials. If control determines at 620 that the subsequent request denials have reached or exceeded the threshold, control proceeds to obtain data for the subsequent request denials at 624. Control then generates model feature vectors for the subsequent request denials at 612, and retrains the XGBoost model at 616 using the subsequent request denials. In this manner, the XGBoost model can be continuously updated and retrained over time as additional request denials their way through the appeal process.

CONCLUSION

The foregoing description is merely illustrative in nature and is in no way intended to limit the disclosure, its application, or uses. The broad teachings of the disclosure can be implemented in a variety of forms. Therefore, while this disclosure includes particular examples, the true scope of the disclosure should not be so limited since other modifications will become apparent upon a study of the drawings, the specification, and the following claims. It should be understood that one or more steps within a method may be executed in different order (or concurrently) without altering the principles of the present disclosure. Further, although each of the embodiments is described above as having certain features, any one or more of those features described with respect to any embodiment of the disclosure can be implemented in and/or combined with features of any of the other embodiments, even if that combination is not explicitly described. In other words, the described embodiments are not mutually exclusive, and permutations of one or more embodiments with one another remain within the scope of this disclosure.

Spatial and functional relationships between elements (for example, between modules) are described using various terms, including "connected," "engaged," "interfaced," and "coupled." Unless explicitly described as being "direct," when a relationship between first and second elements is described in the above disclosure, that relationship encompasses a direct relationship where no other intervening elements are present between the first and second elements, and also an indirect relationship where one or more intervening elements are present (either spatially or functionally) between the first and second elements.

The phrase at least one of A, B, and C should be construed to mean a logical (A OR B OR C), using a non-exclusive logical OR, and should not be construed to mean "at least one of A, at least one of B, and at least one of C." The term "set" does not necessarily exclude the empty set. The term "non-empty set" may be used to indicate exclusion of the empty set. The term "subset" does not necessarily require a proper subset. In other words, a first subset of a first set may be coextensive with (equal to) the first set.

In the figures, the direction of an arrow, as indicated by the arrowhead, generally demonstrates the flow of information (such as data or instructions) that is of interest to the illustration. For example, when element A and element B exchange a variety of information but information transmitted from element A to element B is relevant to the illustration, the arrow may point from element A to element B. This unidirectional arrow does not imply that no other information is transmitted from element B to element A. Further, for information sent from element A to element B, element B may send requests for, or receipt acknowledgements of, the information to element A.

In this application, including the definitions below, the term "module" or the term "controller" may be replaced with the term "circuit." The term "module" may refer to, be part of, or include processor hardware (shared, dedicated, or group) that executes code and memory hardware (shared, dedicated, or group) that stores code executed by the processor hardware.

The module may include one or more interface circuits. In some examples, the interface circuit(s) may implement wired or wireless interfaces that connect to a local area network (LAN) or a wireless personal area network (WPAN). Examples of a LAN are Institute of Electrical and Electronics Engineers (IEEE) Standard 802.11-2016 (also known as the WIFI wireless networking standard) and IEEE Standard 802.3-2015 (also known as the ETHERNET wired networking standard). Examples of a WPAN are IEEE Standard 802.15.4 (including the ZIGBEE standard from the ZigBee Alliance) and, from the Bluetooth Special Interest Group (SIG), the BLUETOOTH wireless networking standard (including Core Specification versions 3.0, 4.0, 4.1, 4.2, 5.0, and 5.1 from the Bluetooth SIG).

The module may communicate with other modules using the interface circuit(s). Although the module may be depicted in the present disclosure as logically communicating directly with other modules, in various implementations the module may actually communicate via a communications system. The communications system includes physical and/or virtual networking equipment such as hubs, switches, routers, and gateways. In some implementations, the communications system connects to or traverses a wide area network (WAN) such as the Internet. For example, the communications system may include multiple LANs connected to each other over the Internet or point-to-point leased lines using technologies including Multiprotocol Label Switching (MPLS) and virtual private networks (VPNs).

In various implementations, the functionality of the module may be distributed among multiple modules that are connected via the communications system. For example, multiple modules may implement the same functionality distributed by a load balancing system. In a further example, the functionality of the module may be split between a server (also known as remote, or cloud) module and a client (or, user) module. For example, the client module may include a native or web application executing on a client device and in network communication with the server module.

The term code, as used above, may include software, firmware, and/or microcode, and may refer to programs, routines, functions, classes, data structures, and/or objects. Shared processor hardware encompasses a single microprocessor that executes some or all code from multiple modules. Group processor hardware encompasses a microprocessor that, in combination with additional microprocessors, executes some or all code from one or more modules. References to multiple microprocessors encompass multiple microprocessors on discrete dies, multiple microprocessors on a single die, multiple cores of a single microprocessor, multiple threads of a single microprocessor, or a combination of the above.

Shared memory hardware encompasses a single memory device that stores some or all code from multiple modules. Group memory hardware encompasses a memory device that, in combination with other memory devices, stores some or all code from one or more modules.

The term memory hardware is a subset of the term computer-readable medium. The term computer-readable medium, as used herein, does not encompass transitory electrical or electromagnetic signals propagating through a medium (such as on a carrier wave); the term computer-readable medium is therefore considered tangible and non-transitory. Non-limiting examples of a non-transitory computer-readable medium are nonvolatile memory devices (such as a flash memory device, an erasable programmable read-only memory device, or a mask read-only memory device), volatile memory devices (such as a static random access memory device or a dynamic random access memory device), magnetic storage media (such as an analog or digital magnetic tape or a hard disk drive), and optical storage media (such as a CD, a DVD, or a Blu-ray Disc).

The apparatuses and methods described in this application may be partially or fully implemented by a special purpose computer created by configuring a general purpose computer to execute one or more particular functions embodied in computer programs. The functional blocks and flowchart elements described above serve as software specifications, which can be translated into the computer programs by the routine work of a skilled technician or programmer.

The computer programs include processor-executable instructions that are stored on at least one non-transitory computer-readable medium. The computer programs may also include or rely on stored data. The computer programs may encompass a basic input/output system (BIOS) that interacts with hardware of the special purpose computer, device drivers that interact with particular devices of the special purpose computer, one or more operating systems, user applications, background services, background applications, etc.

The computer programs may include: (i) descriptive text to be parsed, such as HTML (hypertext markup language), XML (extensible markup language), or JSON (JavaScript Object Notation), (ii) assembly code, (iii) object code generated from source code by a compiler, (iv) source code for execution by an interpreter, (v) source code for compilation and execution by a just-in-time compiler, etc. As examples only, source code may be written using syntax from languages including C, C++, C #, Objective-C, Swift, Haskell, Go, SQL, R, Lisp, Java®, Fortran, Perl, Pascal, Curl, OCaml, JavaScript®, HTML5 (Hypertext Markup Language 5th revision), Ada, ASP (Active Server Pages), PHP (PHP: Hypertext Preprocessor), Scala, Eiffel, Smalltalk, Erlang, Ruby, Flash®, Visual Basic®, Lua, MATLAB, SIMULINK, and Python®.

What is claimed is:

1. A computerized method of automatically processing a medical imaging record using a machine learning model, the method comprising:
  training a machine learning model prediction engine with
    historical medical imaging records to generate likelihood estimates, according to historical feature vector inputs generated from the historical medical imaging records;

receiving a first medical imaging record from a first system, wherein the first medical imaging record is specific to a first entity;

applying a set of specified approval criteria to the first medical imaging record to determine a provisional outcome;

in response to the provisional outcome being positive, transmitting a signal indicating approval to the first system;

in response to the provisional outcome being negative:
   providing data related to the first medical imaging record to a user interface; and
   selectively identifying an exception to the provisional outcome in response to input received by the user interface;

in response to the exception being identified, transmitting the signal indicating approval to the first system;

in response to the exception not being identified:
   generating a feature vector based on the first medical imaging record;
   inputting the feature vector to the machine learning model prediction engine;
   generating, by the machine learning model prediction engine, a likelihood estimate based on the feature vector;
   comparing the generated likelihood estimate to a target threshold; and
   in response to the generated likelihood estimate being greater than the target threshold, transmitting the signal indicating approval to the first system;

receiving an appeal notification from the first entity at the first system; and in response to receiving, at the first system, the appeal notification and the signal indicating approval, responding to the appeal notification according to the signal indicating approval.

2. The method of claim 1 further comprising, in response to the exception not being identified, transmitting the data related to the first medical imaging record via a representational state transfer (REST) application programming interface (API) of a cloud service device in communication with the machine learning model prediction engine.

3. The method of claim 2 further comprising:
   storing, in a normalized database, parameters associated with multiple entities of a specified group including the first entity; and
   performing, on a periodic basis, updating and normalization of the stored parameters for each of the multiple entities,
   wherein generating the likelihood estimate includes obtaining normalized parameters associated with the first entity from the normalization database, and generating the likelihood estimate according to the obtained normalized parameters.

4. The method of claim 3 wherein obtaining the normalized parameters includes querying a structured query language (SQL) data structure in communication with the normalized database, and the method further includes storing the generated likelihood estimate in the SQL data structure.

5. The method of claim 1 further comprising obtaining request data associated with the first medical imaging record, wherein:

the request data includes at least one of entity information data associated with the first entity, physician information data of a physician associated with the first entity, claims data associated with the first entity, health plan data associated with the first entity, and procedure data associated with the first medical imaging record; and generating the feature vector includes generating the feature vector based at least in part on the request data associated with the first medical imaging record.

6. The method of claim 5, wherein the signal indicating approval is transmitted to the first system prior to receiving the appeal notification.

7. The method of claim 1 wherein selectively identifying an exception to the provisional outcome includes:
   receiving, at the user interface, clinical survey responses from a reviewing entity; and
   evaluating the received clinical survey responses to determine whether an exception to the provisional outcome is identified by the reviewing entity.

8. The method of claim 1 wherein training the machine learning model prediction engine includes:
   generating the historical feature vector inputs according to at least one of historical entity data, historical physician data, historical procedure data, and historical appeal data, each of which are associated with the historical medical imaging records; and
   supplying the historical feature vector inputs to the machine learning model prediction engine to train the machine learning model of the machine learning model prediction engine to generate likelihood estimates using supervised learning.

9. The method of claim 8 wherein the machine learning model comprises an extreme gradient boosting (XGBoost) model.

10. The method of claim 9 further comprising converting the XGBoost model to a linear model including multiple parameters for generating the likelihood estimate.

11. A computer system for automatically processing a medical imaging record using a machine learning model, the computer system comprising:
   memory hardware configured to store a machine learning model prediction engine, historical medical imaging records, and computer-executable instructions; and
   processor hardware configured to execute the instructions, wherein the instructions include:
   training the machine learning model prediction engine with the historical medical imaging records to generate likelihood estimates, according to historical feature vector inputs generated from the historical medical imaging records;
   receiving a first medical imaging record from a first system, wherein the first medical imaging record is specific to a first entity;
   applying a set of specified approval criteria to the first medical imaging record to determine a provisional outcome;
   in response to the provisional outcome being positive, transmitting a signal indicating approval to the first system;
   in response to the provisional outcome being negative:
      providing data related to the first medical imaging record to a user interface; and
      selectively identifying an exception to the provisional outcome in response to input received by the user interface;
   in response to the exception being identified, transmitting the signal indicating approval to the first system;

in response to the exception not being identified:
  generating a feature vector based on the first medical imaging record;
  inputting the feature vector to the machine learning model prediction engine;
  generating, by the machine learning model prediction engine, a likelihood estimate based on the feature vector;
  comparing the generated likelihood estimate to a target threshold; and
  in response to the generated likelihood estimate being greater than the target threshold, transmitting the signal indicating approval to the first system;
receiving an appeal notification from the first entity at the first system; and
in response to receiving, at the first system, the appeal notification and the signal indicating approval, responding to the appeal notification according to the signal indicating approval.

12. The computer system of claim 11 wherein the instructions further include, in response to the exception not being identified, transmitting the data related to the first medical imaging record via a representational state transfer (REST) application programming interface (API) of a cloud service device in communication with the machine learning model prediction engine.

13. The computer system of claim 12 wherein the instructions further include:
  storing, in a normalized database, parameters associated with multiple entities of a specified group including the first entity; and
  performing, on a periodic basis, updating and normalization of the stored parameters for each of the multiple entities,
  wherein the generating the likelihood estimate includes obtaining normalized parameters associated with the first entity from the normalization database, and generating the likelihood estimate according to the obtained normalized parameters.

14. The computer system of claim 13 wherein the obtaining the normalized parameters includes querying a structured query language (SQL) data structure in communication with the normalized database, and the instructions further include storing the generated likelihood estimate in the SQL data structure.

15. The computer system of claim 11 wherein:
  the instructions further include obtaining request data associated with the first medical imaging record, wherein:
  the request data includes at least one of entity information data associated with the first entity, physician information data of a physician associated with the first entity, claims data associated with the first entity, health plan data associated with the first entity, and procedure data associated with the first medical imaging record; and
  the generating the feature vector includes generating the feature vector based at least in part on the request data associated with the first medical imaging record.

16. The computer system of claim 15, wherein the signal indicating approval is transmitted to the first system prior to receiving the appeal notification.

17. The computer system of claim 11 wherein the selectively identifying an exception to the provisional outcome includes:
  receiving, at the user interface, clinical survey responses from a reviewing entity; and
  evaluating the received clinical survey responses to determine whether an exception to the provisional outcome is identified by the reviewing entity.

18. The computer system of claim 11 wherein the training the machine learning model prediction engine includes:
  generating the historical feature vector inputs according to at least one of historical entity data, historical physician data, historical procedure data, and historical appeal data, each of which are associated with the historical medical imaging records; and
  supplying the historical feature vector inputs to the machine learning model prediction engine to train the machine learning model of the machine learning model prediction engine to generate likelihood estimates using supervised learning.

* * * * *